United States Patent
Jaga et al.

(10) Patent No.: US 9,880,176 B2
(45) Date of Patent: Jan. 30, 2018

(54) METHOD FOR DETERMINING THE GLYCOSYLATION OF AN ANTIBODY

(75) Inventors: Delphine Jaga, Lirac (FR); Hamed Mokrane, Les Angles (FR); Stéphane Martinez, Villeneuve les a Vignons (FR); Michel Fink, Bagnols sur Ceze (FR)

(73) Assignee: CISBIO BIOASSAYS, Codolet (FR)

( * ) Notice: Subject to any disclaimer, the term of this patent is extended or adjusted under 35 U.S.C. 154(b) by 482 days.

(21) Appl. No.: 14/345,176

(22) PCT Filed: Sep. 13, 2012

(86) PCT No.: PCT/FR2012/052049
§ 371 (c)(1),
(2), (4) Date: Oct. 2, 2014

(87) PCT Pub. No.: WO2013/038113
PCT Pub. Date: Mar. 21, 2013

(65) Prior Publication Data
US 2015/0024410 A1    Jan. 22, 2015

(30) Foreign Application Priority Data
Sep. 16, 2011 (FR) ..................... 11 58245

(51) Int. Cl.
*G01N 33/58* (2006.01)
*G01N 33/68* (2006.01)

(52) U.S. Cl.
CPC ....... *G01N 33/6854* (2013.01); *G01N 33/582* (2013.01); *G01N 2400/02* (2013.01); *G01N 2440/38* (2013.01)

(58) Field of Classification Search
CPC ............ G01N 33/582; G01N 21/6428; G01N 33/6854; G01N 33/56972; G01N 2333/70535; G01N 2400/02; G01N 33/58; C07K 2317/52; C07K 16/00; C07K 2317/92; C07K 2317/24; C07K 2317/71; C07K 2317/526
See application file for complete search history.

(56) References Cited

U.S. PATENT DOCUMENTS

| | | |
|---|---|---|
| 4,637,988 A | 1/1987 | Hinshaw et al. |
| 4,670,572 A | 6/1987 | Hinshaw et al. |
| 4,761,481 A | 8/1988 | Hale et al. |
| 4,794,191 A | 12/1988 | Hinshaw et al. |
| 4,801,722 A | 1/1989 | Hale et al. |
| 4,837,169 A | 6/1989 | Toner |
| 4,859,777 A | 8/1989 | Toner |
| 5,032,677 A | 7/1991 | Hale et al. |
| 5,055,578 A | 10/1991 | Hale et al. |
| 5,106,957 A | 4/1992 | Hale et al. |
| 5,116,989 A | 5/1992 | Hale et al. |
| 5,202,423 A | 4/1993 | Kankare et al. |
| 5,316,909 A | 5/1994 | Xu |
| 5,324,825 A | 6/1994 | Kankare et al. |
| 5,622,821 A | 4/1997 | Selvin et al. |
| 2009/0176220 A1 | 7/2009 | Dhainaut et al. |

FOREIGN PATENT DOCUMENTS

| | | |
|---|---|---|
| EP | 0180492 | 5/1986 |
| EP | 0321353 | 6/1989 |
| EP | 0403593 | 12/1990 |
| EP | 0601113 | 6/1994 |
| EP | 1154990 | 11/2001 |
| EP | 1154991 | 11/2001 |
| EP | 1298219 | 4/2003 |
| EP | 2169404 | 3/2010 |
| FR | 2844521 | 3/2004 |
| WO | 90/00550 | 1/1990 |
| WO | 93/05049 | 3/1993 |
| WO | 00/48990 | 8/2000 |
| WO | 00/48991 | 8/2000 |
| WO | 01/96877 | 12/2001 |
| WO | 2004/031404 | 4/2004 |
| WO | 2004/072232 | 8/2004 |
| WO | 2007/026099 | 3/2007 |
| WO | 2007/080274 | 7/2007 |
| WO | 2008/063721 | 5/2008 |

OTHER PUBLICATIONS

Joseph R. Lakowicz (Principles of fluorescence spectroscopy, 2nd edition (1999).*
Shields et al., The Journal of Biological Chemistry vol. 276 No. 9 pp. 6591-6604.*
Ferrara et al , PNAS Aug. 2011, vol. 108 No. 31, p. 12671.*
Nimmerjam et al. Science 2005, 310 (5753):1510-2, Abstract).*
Larson et al. (Application note Bio therapeutics, Feb. 2012.*
Adams et al.: "New Biarsenical Ligands and Tetracysteine Motifs for Protein Labeling in Vitro and in Vivo: Synthesis and Biological Applications"; J. Am. Chem. Soc. (2002), vol. 124, pp. 6063-6076.
Ford et al.: "Using Biacore to study Fc receptor function and its inhibition by small peptide ligands"; Biacore Journal—No. 1, 2003, pp. 15-17.
Gautier et al.: "An Engineered Protein Tag for Multiprotein Labeling in Living Cells"; Chemistry & Biology 15, 2008, pp. 128-136.
George et al.: "Specific Labeling of Cell Surface Proteins with Chemically Diverse Compounds"; J. Am. Chem. Soc., 2004, vol. 162, pp. 8896-8897.

(Continued)

*Primary Examiner* — Tracy Vivlemore
*Assistant Examiner* — Carmencita M Belei
(74) *Attorney, Agent, or Firm* — Hamre, Schumann, Mueller & Larson, P.C.

(57) ABSTRACT

The invention relates to a method for detecting the binding of an antibody to an Fc receptor present on the surface of a cell as well as to a method for determining the level of glycosylation of an antibody.

The invention also relates to a reagent kit for carrying out these methods.

1 Claim, 5 Drawing Sheets

(56) References Cited

OTHER PUBLICATIONS

Griffin et al.: "Specific Covalent Labeling of Recombinant Protein Molecules Inside Lives Cells"; Science, 1998, vol. 281, pp. 269-272.

Gronemeyer et al.: " Directed evolution of O6-alkylguanine-DNA alkyltransferase for applications in protein labeling"; Protein Engineering, Design & Selection, 2006, vol. 19, No. 7, pp. 309-316.

Juillerat et al.: "Directed Evolution of O6-Alkylguanine-DNA Alkyltransferase for Efficient Labeling of Fusion Proteins with Small Molecules In Vivo"; Chemistry & Biology, 2003, vol. 10, pp. 313-317.

J. R. Lakowicz: "Principles of Fluorescence Spectroscopy"; 3rd edition (2006), pp. 443-453.

Latva et al.: "Correlation between the lowest triplet state energy level of the ligand and lanthanide (III) luminescence quantum yield"; Journal of Luminescence 75 (1997), pp. 149-169.

McCann et al.: "Peptide tags for labeling membrane proteins in live cells with multiple fluorophores"; BioTechniques, 2005, vol. 38, No. 6, pp. 945-952.

Poole et al.: "Synthesis and characterisation of highly emissive and kinetically stable lanthanide complexes suitable for usage 'in cellulo'"; Org. Biomol. Chem., 2005, 3, pp. 1013-1024.

Suzuki et al.: A Nonfucosylated Anti-HER2 Antibody Augments Antobody-Dependent Cellular Cytotoxicity in Breast Cancer Patients; Clin Cander Res. 2007; 13(6), pp. 1875-1882.

Yamane-Ohnuki et al.: "Production of therapeutic antobodies with controlled fucosylation"; Mabs. 2009, 1(3), pp. 230-236.

Shields et al.: "Lack of Fucose on Human IgG1 N-Linked Oligosaccharide Improves Binding to Human FcγRIII and Antibody-dependent Cellular Toxicity"; The Journal of Biological Chemistry, vol. 277, No. 30, Issue of Jul. 26, 2002, pp. 26733-26740.

International Search Report; PCT/FR2012/052049, dated Sep. 13, 2012 (5 pages—submitted Mar. 14, 2014).

\* cited by examiner

METHOD FOR DETERMINING THE GLYCOSYLATION OF AN ANTIBODY

FIELD OF THE INVENTION

The invention relates to a method for detecting the binding of an antibody to a receptor for the crystallizable Fc fragments (hereinafter "Fc receptors" or FcR) present on the surface of a cell as well as a method for determining the level of glycosylation of an antibody.

PRIOR ART

For some years now, recombinant monoclonal antibodies have permitted a therapeutic revolution. Although their clinical efficacy no longer requires any proof, still little is known about their manner of action in patients. The therapeutic effect of antibodies targeting membrane antigens notably involves the recruitment of effector cells expressing receptors for the crystallizable fragment of the antibodies (hereinafter, "Fc receptors").

The Fc receptors are proteins present on the surface of certain cells contributing to the functions of the immune system, in particular NK ("natural killer") cells, macrophages, neutrophils and mastocytes. Their name comes from their capacity for binding to the Fc (crystallizable fragment) region of the antibodies. There are several types of them, which are classified according to the type of antibody that they recognize: the Fc gamma receptors (FcγR) bind to IgGs, the Fc alpha receptor (FcαR) binds to IgAs and the Fc epsilon receptors (FcεR) bind to IgEs.

Binding of the Fc receptor to an antibody triggers various mechanisms depending on the nature of the cell on which this receptor is expressed. Table 1 is a synopsis of the cellular distribution of the different Fc receptors and the mechanisms triggered by binding of the receptor to an antibody.

TABLE 1

| Receptor | Antibody recognized | Cellular distribution | Effet following binding to the antibody |
| --- | --- | --- | --- |
| FcγRI (CD64) | IgG1 and IgG3 | Macrophages Neutrophils Eosinophils Dendritic cells | phagocytosis cellular activation generation of reactive oxygen destruction of microbes |
| FcγRIIA (CD32) | IgG | Macrophages Neutrophils Eosinophils Platelets Langerhans cells | phagocytosis degranulation (eosinophils) |
| FcγRIIB1 (CD32) | IgG | B lymphocytes Mastocytes | no phagocytosis inhibition of cellular activity |
| FCγRIIB2 (CD32) | IgG | Macrophages Neutrophils Eosinophils | phagocytosis inhibition of cellular activity |
| FcγRIIIA (CD16A) | IgG | NK cells Macrophages (certain tissues) | induction of antibody-dependent cellular cytotoxicity (ADCC) induction of release of cytokines by the macrophages |
| FcγRIIIB (CD16b) | IgG | Eosinophils Macrophages Neutrophils Mastocytes Follicular dendritic cells | destruction of microbes |
| FcεRI | IgE | Mastocytes Eosinophils Basophils Langerhans cells | degranulation |
| FcεRII (CD23) | IgE | B lymphocytes Eosinophils Langerhans cells | adhesion molecule possible |
| FcαRI (CD89) | IgA | Monocytes Macrophages Neutrophils Eosinophils | phagocytosis destruction of microbes |
| Fcα/μR | IgA and IgM | B lymphocytes Mesangial cells Macrophages | endocytosis destruction of microbes |
| FcRn | IgG | Monocytes Macrophages Dendritic cells Epithelial cells Endothelial cells Hepatocytes | transfer of IgG from mother to fetus via the placenta transfer of IgG from mother to child in the milk Protects IgG against degradation |

In view of the importance of the mechanisms associated with binding of the Fc receptors to antibodies, it would be particularly advantageous to be able to detect this binding when these receptors are in a cellular context, in particular in the context of the development of antibodies or Fc fragments for diagnostic or therapeutic purposes.

Therapeutic antibodies triggering the ADCC mechanism are currently being marketed (Herceptin®, Cetuximab®) and are indicated in the treatment of certain cancers: the Fc fragment of these antibodies binds to an Fc receptor present on the NK cells, whereas the variable domains of these antibodies recognize an antigen present on tumor cells (Herceptin: Her2, Cetuximab: Her1). The binding of these antibodies simultaneously to an NK cell and to a cancer cell leads notably to destruction of the latter by activation of the ADCC mechanism.

It is moreover known that glycosylation of the Fc fragment of antibodies influences the affinity of these antibodies for the FcRs, and therefore their ability to recruit effector cells. In particular, modified therapeutic antibodies bearing few or no fucose residues at the level of the N-glycan groups of the Fc fragment provoke a strong ADCC response at low concentrations and with much better efficacy in comparison with their fucosylated equivalents (Shields et al., 3 Biol. Chem. 2002 Jul. 26; 277(30): 26733-40, Suzuki et al. Clin Cancer Res. 2007 Mar. 15; 13(6): 1875-82). The binding of the antibodies to the FcRs was measured in these studies by an assay of the ELISA type (acronym of "enzyme-linked immunosorbent assay"), or else functionally, by measuring the ADCC response.

In general, a method for detecting the binding of potentially therapeutic antibodies to the Fc receptors expressed by an intact cell would be a valuable tool for developing therapeutic antibodies, or else for studying immune system mechanisms mediated by the Fc receptors. The techniques currently available for studying the binding of antibodies to the Fc receptors are relatively tedious.

The system marketed under the name Biacore® allows detection of interactions between two binding partners and is based on the phenomenon of surface plasmon resonance. This system has been used for studying the effect of the glycosylation of Fc fragments of antibodies on their binding to the FcγRIII receptor. It requires immobilization of the Fc receptor or else of a fragment of the Fc domain of the antibody being tested on a microchip, capable of generating a signal that depends on the refractive index at its surface (Biacore Journal Number 1, 2003, 15-17). This approach has several drawbacks, notably a critical step of fixation of one of the binding partners on the surface of the microchip, the need for expensive equipment that requires a certain level of expertise, and the fact that the technique cannot be used for working with living cells expressing the Fc receptor under investigation. Moreover, this approach also does not supply information regarding possible binding of the antibody tested to its antigen in its cellular conformation.

French patent application FR2844521 describes an approach according to which an antibody is contacted with cells expressing the CD16 receptor in the presence of the antigen of said antibody, and at least one cytokine produced by the cells is measured, an increase in the amount of cytokine being representative of the activation of said cells. This technique does not allow direct measurement of the binding of the antibody to the FcR. It also requires a step of centrifugation of the supernatant for detecting the cytokines secreted by the cells.

European patent application EP 1 298 219 describes a method for determining the effect of the Fc fragment of an antibody on a cell expressing an FcR, consisting of immobilizing said antibody on a solid support, cultivating cells expressing said receptor in the presence of said antibody, and measuring any effect of the FcR in the presence of the antibody. In this method, the activation of the FcR is also measured indirectly by detecting the production of cytokines by the cell. This technique has the same drawbacks as that described in application FR2844521, notably a centrifugation step.

US patent application US 2009/0176220 presents a variant of the aforementioned approaches, consisting of contacting cells expressing FcRs with antibodies that have previously been submitted to aggregation. As in the aforementioned techniques, the activation of the cells is determined by measuring cytokines secreted by the cell.

The company Cisbio Bioassays markets a product range under the name TAG-LITE®, for labeling proteins expressed by cells with fluorescent compounds, as well as FRET partner fluorescent compounds (HTRF®). Since the phenomenon of FRET between an energy donor compound and an acceptor compound depends on the distance between these two compounds, the products in the TAG-LITE® range can be used for studying molecular interactions in a cellular context. One of the applications of this technique is for studying the interaction between a receptor coupled to proteins G (RCPG) labeled with a FRET partner, with its ligand labeled with a second FRET partner. This approach makes it possible for example to perform competitive assays for evaluating the binding of potential new ligands of these RCPGs. Another example of application of these products is investigation of the dimerization of RCPGs labeled with FRET partner compounds.

No method exists at present for direct measurement of the binding of an antibody to an Fc receptor expressed on the surface of an intact cell. The existing techniques have several drawbacks: indirect assays of cytokines secreted by the cells, centrifugation steps that are rather unsuitable for automated use, or else the use of approaches that require tedious preliminary steps and take a relatively long time. Moreover, these techniques do not allow information to be obtained easily and quickly concerning the level of glycosylation of a given antibody and its effect on binding to the Fc receptors.

The inventors have developed a method for resolving these problems.

DESCRIPTION

Figure 1:
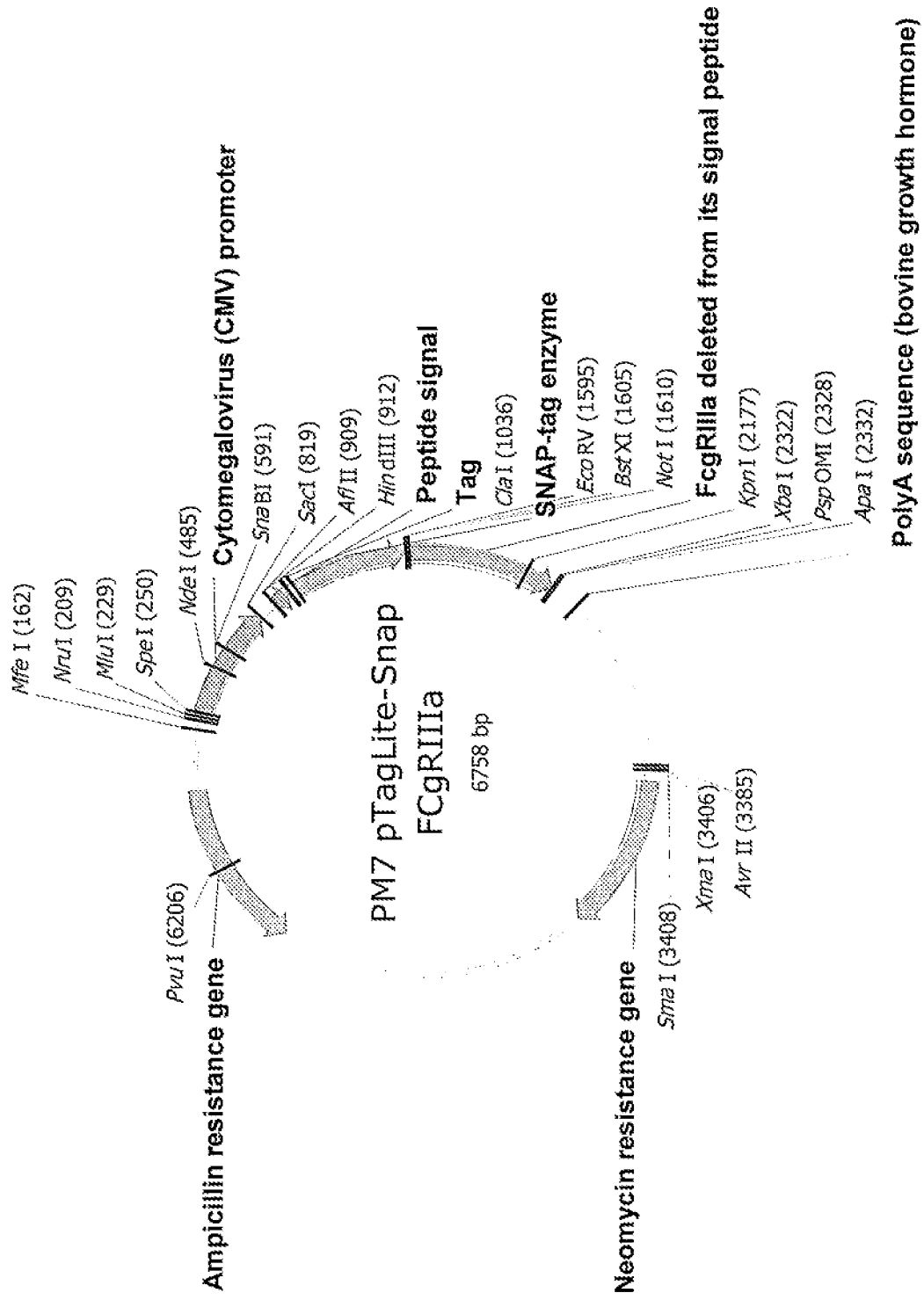
FIG. 1 is a plasmid coding FcgammaRIIIa.

The invention consists of an in vitro method for determining the binding of an antibody to an Fc receptor expressed in cell membranes or intact cells present in a measurement medium, comprising the following steps:
(i) direct or indirect labeling of said Fc receptor with the first member of a pair of FRET partners, or else introduction, into the medium, of cell membranes or intact cells whose Fc receptors were previously labeled directly with the first member of a pair of FRET partners;
(ii) adding said antibody, labeled directly or indirectly with the second member of said pair of FRET partners, to the measurement medium;
(iii) measuring the FRET signal, the existence of a FRET signal being representative of the binding of the antibody to the Fc receptor.

This method can notably be used for determining the dissociation constant of an Fc receptor-antibody complex. In this case, it is repeated with different antibody concentrations, in particular increasing antibody concentrations, in order to establish a saturation curve, representing the evolution of the FRET signal as a function of the antibody concentration. This curve can be used for determining the dissociation constant ("Kd") corresponding to the antibody concentration at 50% saturation of the Fc receptor.

A competitive assay format constitutes a preferred implementation of the invention. In this implementation, the invention consists of an in vitro method for determining the binding of an antibody (hereinafter "competing antibody") to an Fc receptor expressed in cell membranes or intact cells present in a measurement medium, by competition with a reference antibody, comprising the following steps:
(i) direct or indirect labeling of said Fc receptor with the first member of a pair of FRET partners, or else introducing, into the medium, cell membranes or intact cells whose Fc receptors were previously labeled directly with the first member of a pair of FRET partners;
(ii) adding the competing antibody to the measurement medium;
(iii) adding a reference antibody, labeled directly or indirectly with the second member of said pair of FRET partners, to the measurement medium;
(iv) measuring the FRET signal, a decrease in the signal measured in the presence of the competing antibody relative to that measured in its absence being representative of the binding of this antibody to the Fc receptor.

Steps (i), (ii) and (iii) are preferably employed in this order, but it is possible to bring the various elements into contact in a different order (for example ((i), (iii), (ii)), or else simultaneously.

Step (iv) is carried out after an incubation time, which can range from a few minutes (for example 3, 4, or 5 minutes), to several hours (for example from 1 to 20 hours).

If the concentration of the competing antibody is known, then the signal obtained in step (iv) can be compared with the signal measured when the method is carried out with an unlabeled reference antibody instead of the competing antibody, and a conclusion can be drawn regarding the affinity of the latter for the Fc receptor. In particular, at equal concentration, if the FRET signal measured in the presence of the competing antibody is lower than that measured in the presence of the unlabeled reference antibody, the competing antibody has a better affinity than the latter, and vice versa. The unlabeled reference antibody can be the same as that in step (iii), or else can be another antibody with which it is wished to compare the competing antibody.

Moreover, when the above method of competitive assay is reproduced in the presence of different amounts of test antibody and a fixed amount of reference antibody, the results obtained make it possible to determine the EC50 of the competing antibody. The EC50 of the antibody can be compared with that of the reference antibody, the antibody having the lowest EC50 being the one having the best affinity for the Fc receptor. "EC50" means the concentration for reaching 50% of a given effect. Here, the EC50 of a competing antibody will correspond to the concentration of this antibody inhibiting 50% of the binding of the reference antibody to the Fc receptor. A person skilled in the art is familiar with this concept, and software is available for calculating the EC50s automatically from the results obtained in the foregoing implementation.

It should be noted that the method according to the invention does not require the competing antibody to be used in purified form: it can be included in a mixture, for example a culture supernatant of cells producing this antibody. One of the advantages of the method of the invention is that it is possible to study unpurified antibodies, since it does not require tedious steps of preparation of the antibodies to be tested.

The above methods are carried out with Fc receptors expressed in cell membranes or intact cells. These membranes can be prepared conventionally from cells submitted to a chemical or mechanical treatment. The term "cell membranes" includes the membranes of intact cells, and carrying out the invention with intact cells is particularly advantageous and preferred since the method is then carried out in a context that is relatively close to biological reality.

"Reference antibody" means an antibody that is definitely known to bind to the Fc receptor. Thus, if the Fc receptor is a gamma Fc receptor (FcγR), the reference antibody can be any antibody of the IgG class, whatever its epitope specificity. Moreover, if the Fc receptor is an alpha or epsilon Fc receptor, the reference antibody can be any antibody of the IgA or IgE class, respectively.

Unexpectedly, the method according to the invention is sufficiently sensitive to permit observation of variations in affinity when certain modifications are made to the antibodies. More precisely, the inventors discovered that modifications that are known to increase or decrease the affinity of an antibody for an Fc receptor are correlated with variations of EC50 measured with the method according to the invention.

Thus, in a particular embodiment, the reference antibody and the competing antibody differ notably in that the latter was produced by a method, or else has undergone a treatment, aiming to alter the level of glycosylation of its Fc fragment.

In particular and in a preferred embodiment, the test antibody was produced by a method, or else underwent a treatment, aiming to alter the fucosylation of its Fc fragment. Such methods and treatments are known by a person skilled in the art and are used for improving the efficacy of certain therapeutic antibodies. These treatments, described inter alia by Yamane-Ohnuki et al. (MAbs. 2009 May-June; 1(3): 230-6), are of three types:

Method of production of antibodies by genetic engineering in eukaryotic organisms (yeasts) or plant cells whose N-glycosylation pathways have been modified to make them more like those of mammals: this approach consists of deactivating certain genes involved in the mechanisms of N-glycosylation of these organisms and of introducing others that are specific to the N-glycosylation pathways of mammals.

Method of production of antibodies by genetic engineering in mammalian cells (1) naturally having limited intrinsic activity of α-1,6 fucosylation, or (2) in which the mechanisms of α-1,6 fucosylation have been inhibited by the introduction of small strands of interfering RNA (known by the acronym siRNA), or else (3) in which DNA coding for β-1,4-N-acetylglucosaminyl-transferase (GnTIII) and that coding for α-mannosidase II (ManII) of the Golgi have been introduced, or finally (4) whose α-1,6 fucosylation function has been inhibited at the level of the genomic locus responsible for this glycosylation pathway.

Control of antibody fucosylation in vitro, by treatment with enzymes catalyzing the fucosylation of nonfucosylated proteins or else fucosylases capable of cleaving the sugar residues of fucosylated proteins.

The invention allows easy testing of the antibodies thus obtained for their capacity for binding to the Fc receptors, which constitutes very valuable information as it is indicative of the potential therapeutic efficacy of these antibodies.

One variant of the invention makes it possible to determine the level of glycosylation of a test antibody. It is characterized in that it comprises the following steps:

applying the method of competitive assay with several competing antibodies having known levels of glycosylation or of deglycosylation, this method being reproduced in the presence of different amounts of each competing antibody and a fixed amount of reference antibody then applying the method of competitive assay but this time with the test antibody as competing antibody, this method being reproduced in the presence of different amounts of test antibody and a fixed amount of reference antibody, and determining the level of glycosylation of the test antibody by comparing its EC50 with that of each of the competing antibodies whose levels of glycosylation or of deglycosylation are known.

This method makes it possible in particular to determine the level of fucosylation of an antibody.

These latter embodiments for studying antibodies whose glycosylation or fucosylation has been limited in some way or other are particularly suitable for the case when the Fc receptor is a gamma Fc receptor and in particular the CD16a receptor or a variant thereof, whose binding to the Fc fragments of the antibodies of the IgG1 class is known to be related to the level of fucosylation of these antibodies. Since the level of fucosylation of the antibodies is directly correlated with the intensity of the response of the effector cell, for example with the intensity of the ADCC response, this method makes it possible to predict the capacity of the antibody for triggering a response via the effector cell.

In the above embodiments, cell membranes whose receptors have been labeled beforehand (and the cell membranes optionally frozen) can also be used, and step (i) then consists of introducing, into the measurement medium, cell membranes whose Fc receptors were labeled beforehand directly with the first member of a pair of FRET partners. In the case when frozen labeled cells are used, they will have been washed after thawing and before being added to the measurement medium.

The terms used above have the following meanings:

"Pair of FRET partners": this expression denotes a pair consisting of a fluorescent energy donor compound (hereinafter "fluorescent donor compound") and an energy acceptor compound (hereinafter "acceptor compound"); when they are close to one another and when they are excited at the excitation wavelength of the fluorescent donor compound, these compounds emit a FRET signal. It is known that for two fluorescent compounds to be FRET partners, the emission spectrum of the fluorescent donor compound must partially cover the excitation spectrum of the acceptor compound.

"FRET signal": denotes any measurable signal representative of a FRET between a fluorescent donor compound and an acceptor compound. A FRET signal can therefore be a change in the luminescence intensity or lifetime of the fluorescent donor compound or of the acceptor compound when the latter is fluorescent.

"Measurement medium": denotes the contents of the well of a plate, of a test tube or of any other suitable container for mixing cells or cell membranes with the reagents required for carrying out the invention.

The Fc receptor is selected from the receptors in Table 1, and is preferably the CD16a receptor (FcγRIIIa) or a variant thereof. Several variants of this receptor are known, in particular the natural variants L66H, L66R, G147D, Y158H, F203S, F176V (or F158V in certain publications). In a preferred embodiment, variant V158 (or V176) is used. In another embodiment it is variant F158 (or F176).

The various means for labeling the Fc receptor are described below, but preferably the Fc receptor is labeled directly via a suicide enzyme, and this enzyme can in particular be selected from: the mutants of dehalogenase, or a fragment of the acyl transport protein, the mutants of O6-alkylguanine DNA alkyltransferase, the latter being preferred. Moreover, as pointed out, this method of labeling the Fc receptor means that the cells have undergone a prior treatment permitting expression of a fusion protein comprising the Fc receptor and the suicide enzyme. Labeling will be carried out by adding the substrate of the enzyme, conjugated to one of the members of the pair of FRET partners.

Moreover, the means for labeling the fluorophore-labeled antibody are described below but preferably this antibody is labeled directly, by covalent binding to one of the FRET partners.

In a particular embodiment, the Fc receptor is labeled with the acceptor compound and the antibody with the donor compound. In another embodiment, the Fc receptor is labeled with the donor compound and the antibody with the acceptor compound. The latter embodiment is preferred.

Labeling of the Fc Receptor (a) Coupling of the Fc Receptor to a Donor or an Acceptor Indirectly (Noncovalently)

The donor or the acceptor can be coupled to the Fc receptor via a protein capable of associating with the Fc receptor, this protein itself being labeled directly or indirectly with the first member of a pair of FRET partners. It is for example known that the FcγRIIIA (CD16a) receptor is associated in the cell membrane with the gamma chain of the FcεRI receptor or with the zeta subunit of CD3; the CD16a receptor can thus be labeled indirectly via these gamma or zeta chains, which themselves are labeled directly with a fluorescent compound.

The donor or the acceptor can be coupled to the Fc receptor via a pair of binding partners, at least one of which is of protein nature. In this approach, the Fc receptor is fused with the binding partner of protein nature by the classical techniques of molecular biology (construction of an expression vector comprising a nucleotide sequence coding for the Fc receptor, fused with that coding for the protein binding partner, and insertion of the expression vector in the cell). The donor or the acceptor is conjugated covalently to the other binding partner, which is called coupling agent here, which will then be added to the extracellular medium. Recognition of the binding partners allows indirect labeling of the Fc receptor with the donor or the acceptor.

As nonlimiting examples of binding partners of this type, we may mention:

The pair consisting of a specific antibody of an epitope naturally present on the Fc receptor, labeled with a fluorescent compound, and this epitope. When this method of labeling is used, it is advisable to check that the binding of this antibody to this epitope does not interfere with the binding of the Fc receptor to the Fc fragments of antibodies. Moreover, in this embodiment, it is advisable to avoid using an antibody whose constant fragment might be recognized by the Fc receptor of interest.

The pair consisting of the sequence cysteine-cysteine-X-X-cysteine-cysteine (SEQ ID No. 1) in which X is any amino acid and a biarsenic compound. These biarsenic compounds can easily be labeled with an organic molecule of the fluorescein or rhodamine type (see B. A. Griffin et al. (1998) Science. 1998, 281, 269-271 and S. A. Adams et al. (2002) J. Am. Chem. Soc. 2002, 124, 6063-6076 for details on the technology).

The BTX (bungarotoxin) peptide, a compound of 13 amino acids that is recognized by bungarotoxin (BTX), can be coupled to a fluorescent molecule (see C. M. McCann et al. (2005), Biotechnique (2005), 38, 945-952).

The streptavidin (or avidin)/biotin pair: the binding sequence of streptavidin (SBP-Tag) is a sequence formed by 38 amino acids that has high affinity for biotin and can be labeled beforehand with a donor or an acceptor (see C. M. McCann et al. (2005), Biotechnique (2005), 38, 945-952).

The sequence of the enzyme dihydrofolate reductase from E. coli (eDHFR), which binds ligands specifically and with high affinity, such as trimethoprim, on which the donor or the acceptor can be grafted by the technology called "Ligand link Universal labeling technology" of the company Active Motif.

Tag/antitag pairs are binding partners frequently used for labeling proteins. The term "tag" denotes a small protein "label" consisting of an amino acid sequence, generally but not necessarily quite short (less than 15 amino acids), which is fused to the Fc receptor. The term "antitag" denotes an antibody that binds specifically to said "tag". In this embodiment, the "antitag" antibody is bound covalently to the donor or to the acceptor. When the antibody thus labeled is added to the extracellular medium, it binds to the "tag" conjugated with the Fc receptor and the "tag/antitag" interaction allows indirect labeling of this protein with the donor or the acceptor. As nonlimiting examples of "tag/antitag" pairs, we may mention the following pairs, the members of which are available commercially: GST/anti-GST antibody in which GST represents glutathione S-transferase or a fragment thereof; 6HIS/anti-6HIS antibody in which 6HIS is a peptide consisting of 6 histidines; Myc/anti-Myc antibody in which Myc is a peptide consisting of amino acids 410-419 of the human protein Myc; FLAG/anti-FLAG antibody in which FLAG is a peptide having the 8 amino acids DYKDDDDK (SEQ ID No. 2); HA/anti-HA antibody in which HA is an epitope of the influenza hemagglutinin, consisting of the 9 amino acids YPYDVPFYA (SEQ ID No. 3). It is clear that the precise nature of the tag is not critical for implementing the invention.

(b) Coupling of the Fc Receptor with a Donor or an Acceptor Covalently

In this approach, the donor or the acceptor is coupled to the Fc receptor with a covalent bond; several techniques have been described and the reagents necessary for carrying them out are available commercially. For this coupling, one of the following techniques can be used:

Formation of a covalent bond at the level of a reactive group present on the Fc receptor, in particular at the level of one of the following groups: the terminal amino group, the carboxylate groups of aspartic and glutamic acids, the amine groups of lysines, the guanidine groups of arginines, the thiol groups of cysteines, the phenol groups of tyrosines, the indole rings of tryptophans, the thioether groups of methionines, the imidazole groups of histidines.

These groups present on the Fc receptor can form a covalent bond with a reactive group carried by the donor or the acceptor. The appropriate reactive groups are known by a person skilled in the art: a donor or the acceptor functionalized with a maleimide group will for example be capable of binding covalently to the thiol groups carried by the cysteines of the protein. Moreover, a donor/acceptor bearing an N-hydroxysuccinimide ester will be capable of attaching covalently to an amine of the membrane receptor.

Use of a suicide enzyme

"Suicide enzyme" means proteins that have an enzyme activity modified by specific mutations that endow them with the capacity for binding a substrate rapidly and covalently. These enzymes are called "suicide enzymes" because each one can only bind a single fluorescent molecule, the activity of the enzyme being blocked by fixation of the substrate. These enzymes consequently constitute a tool of choice for specifically labeling receptors of interest with a ratio of one fluorescent molecule to one protein. In this approach, a suicide enzyme is fused, by the classical techniques of molecular biology, with the Fc receptor—preferably in its N-terminal portion—and the substrate of the enzyme bound covalently to a donor/acceptor is introduced into the extracellular medium. The enzymatic reaction leads to covalent binding of the labeled substrate to the enzyme, and therefore labeling of the Fc receptor with the donor or the acceptor.

The following enzymes may be mentioned as nonlimiting examples:

the mutants of O6-alkylguanine DNA alkyltransferase (AGT). The enzymes SNAP-tag (Juillerat et al., Chemistry & biology, Vol. 10, 313-317 April 2003) and CLIP-tag (Gautier et al., Chemistry and Biology, 15, 128-136, February 2008) marketed by the company Cisbio Bioassays are mutants of human AGT whose substrates are $O^6$-benzylguanine (abbreviated hereinafter as BG) and $O^2$-benzylcytosine (abbreviated hereinafter as BC), respectively. The enzyme N-AGT (Gronemeyer et al. (Protein engineering, design & selection, Vol. 19, no 7, pp 309-3016, 2006)) is another mutant of this enzyme whose reactivity with $O^6$-benzylguanine is better than that of the enzyme SNAP-tag.

the mutants of a dehalogenase (such as the enzyme HaloTag marketed by Promega) which also generates an enzymatic reaction of the suicide type (see WO2004/072232), some of the substrates of which are compounds of the chloroalkane family, in particular the chloroalkanes comprising the —NH—$CH_2CH_2$—O—$CH_2CH_2$—O—$(CH_2)_6$—Cl unit. In this case, the donor/acceptor will be conjugated with this type of unit.

The protein ACP ("Acyl Carrier protein"), an acyl transporter protein, onto which the 4'-phosphopantetheine residue of the coenzyme A on a serine of the ACP is transferred, in the presence of phosphopantetheine transferase (N. George et al., Journal of the American Chemical Society 126 (2004) p 8896-8897). When this approach is used for labeling the Fc receptor with the donor or the acceptor, it is necessary to add phosphopantetheine transferase to the reaction medium. The company NEB markets a fragment of ACP under the trade name "ACP-Tag" for labeling proteins.

When this approach is used for labeling the receptor of interest, the cells are transfected with an expression plasmid comprising the DNA coding for a fusion protein comprising the suicide enzyme and the receptor of interest. This plasmid can also comprise, upstream of the DNA coding for these proteins, the DNA coding for a tag such as for example the FLAG epitope, the myc epitope, or else that of influenza hemagglutinin (HA). These tags are not essential but facilitate manipulation of the fusion protein for purposes of inspection or purification. Transfection is performed by the classical techniques, such as electroporation.

In order to ensure that the fusion protein will be expressed in the cell membrane, it may be useful to include in the expression plasmid, upstream of the sequence coding for the receptor of interest and the suicide enzyme, that coding for a membrane-addressing peptide, such as the T8 signal peptide or the signal peptide of the mGluR5 receptor, use of which for this purpose is known by a person skilled in the art. Finally, it may also be desirable to ensure that the sequence coding for the receptor of interest does not comprise a native membrane-addressing sequence that could be the object of post-translational cleavage of the bond between the receptor of interest and the suicide enzyme: if this is the case, it is preferable not to introduce this domain into the expression plasmid.

Finally, when a suicide enzyme is used for labeling the Fc receptor with the FRET partner, the invention comprises a preliminary step of transfection of the cells with an expression vector comprising the DNA sequence coding for a fusion protein corresponding to the Fc receptor, fused in its N-terminal portion with a suicide enzyme. The techniques of transfection such as electroporation or the use of lipofectamine are known by a person skilled in the art.

The introduction of the substrate of the enzyme conjugated with a FRET partner into the extracellular medium will result in labeling of the receptor of interest with this FRET partner.

The company Cisbio Bioassays markets TAG-LITE® plasmids permitting expression of fusion proteins with the suicide enzymes known by the trade names SNAP-Tag®, CLIP-Tag® and Halotag®. The DNA sequences coding for the Fc receptors in Table 1 are known and are available in databases such as Genbank.

Labeling of the Antibody

The antibody can also be labeled directly or indirectly.

Direct labeling of the antibody with a fluorescent compound can be carried out by the classical methods known by a person skilled in the art, based on the presence of reactive groups on the antibody, in particular the following groups: the terminal amino group, the carboxylate groups of aspartic acid and glutamic acid, the amine groups of lysines, the guanidine groups of arginines, the thiol groups of cysteines, the phenol groups of tyrosines, the indole rings of tryptophans, the thioether groups of methionines, the imidazole groups of histidines.

These groups can form a covalent bond with a reactive group carried by the fluorescent compound. The appropriate reactive groups are known by a person skilled in the art: a donor or acceptor functionalized with a maleimide group will for example be capable of binding covalently to the thiol groups carried by the cysteines of the protein. Moreover, a donor/acceptor bearing an N-hydroxysuccinimide ester will be capable of attaching covalently to an amine present on the antibody.

The antibody can also be labeled with a fluorescent compound indirectly, for example by introducing, into the measurement medium, another antibody, which is itself bound covalently to a fluorescent compound, this second antibody specifically recognizing the first antibody. When this approach is used, it is advisable to select a secondary antibody whose Fc domain will not be recognized by the Fc receptor.

Another very classical means of indirect labeling consists of fixing biotin on the antibody to be labeled, then incubating this biotinylated antibody in the presence of streptavidin labeled with a fluorophore. Biotinylated antibodies are commercially available and the company Cisbio Bioassays markets for example streptavidin labeled with the fluorophore whose trade name is "d2" (ref. 610SADLA).

Since the antibody whose binding to the Fc receptor is to be measured is bound to this receptor via its Fc domain, its variable domains remain available for recognizing the antigen for which they are specific. It is therefore also possible to label the antibody indirectly by introducing the antigen of this antibody into the measurement medium, this antigen being labeled with a fluorescent compound.

Pairs of FRET Partners

According to the invention, the Fc receptors and at least one of the antibodies recognized by these receptors are each labeled with a member of a pair of FRET partners, in particular with a fluorescent donor compound or a fluorescent energy acceptor compound.

FRET is defined as a nonradiative transfer of energy resulting from a dipole-dipole interaction between an energy donor and an energy acceptor. This physical phenomenon requires energetic compatibility between these molecules. This signifies that the emission spectrum of the donor must cover, at least partially, the absorption spectrum of the acceptor. In accordance with Förster's theory, FRET is a process that depends on the distance between the two molecules, donor and acceptor: when these molecules are close together, a FRET signal will be emitted.

Selection of the donor/acceptor pair of fluorophores for obtaining a FRET signal is within the capability of a person skilled in the art. Donor-acceptor pairs usable for studying FRET phenomena are notably described in the work of Joseph R. Lakowicz (Principles of fluorescence spectroscopy, $2^{nd}$ edition 338), which a person skilled in the art will be able to consult.

The energy donor fluorescent compounds that are long-lived (>0.1 ms, preferably between 0.5 and 6 ms), in particular the chelates or cryptates of rare earths, are advantageous since they make it possible to effect time-resolved measurements, i.e. to measure TR-FRET ("Time Resolved FRET") signals without a large part of the background noise emitted by the measurement medium. For this reason and generally they are preferred for carrying out the method according to the invention. Advantageously, these compounds are lanthanide complexes. These complexes (such as chelates or cryptates) are particularly suitable as a member of the energy donor FRET pair.

Complexes of dysprosium ($Dy^{3+}$), of samarium ($Sm^{3+}$), of neodymium ($Nd^{3+}$), of ytterbium ($Yb^{3+}$) or of erbium ($Er^{3+}$) are rare earth complexes that are also suitable for the purposes of the invention, but the complexes of europium ($Eu^{3+}$) and of terbium ($Tb^{3+}$) are particularly preferred.

Numerous rare earth complexes have been described and several are currently marketed by the companies PerkinElmer, Invitrogen and Cisbio Bioassays.

Examples of chelates or cryptates of rare earths suitable for the purposes of the invention are:

The cryptates of lanthanides, comprising one or more pyridine units. These rare earth cryptates are described for example in patents EP 0 180 492, EP 0 321 353, EP 0 601 113 and in international application WO 01/96 877. The cryptates of terbium ($Tb^{3+}$) and of europium ($Eu^{3+}$) are particularly suitable for the purposes of the present invention. Cryptates of lanthanides are marketed by the company Cisbio Bioassays. We may mention, as nonlimiting examples, the europium cryptates with the following formulas (which can be coupled to the compound to be labeled via a reactive group, here for example an $NH_2$ group):

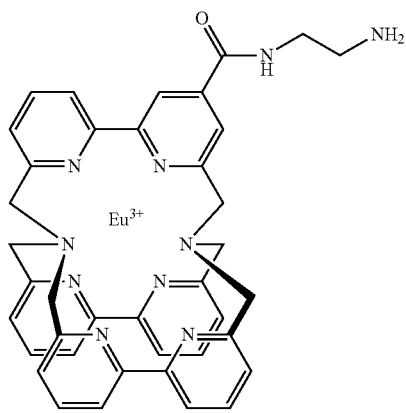

TrisBiPy-Eu

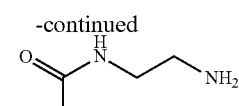

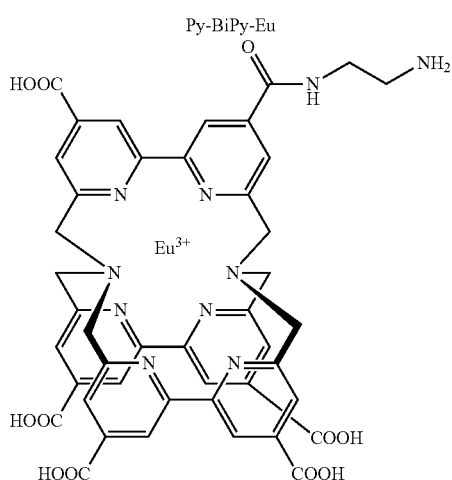

Py-BiPy-Eu

TrisBiPy-tetraacid-Eu

Py-BiPy-tetraacid-Eu

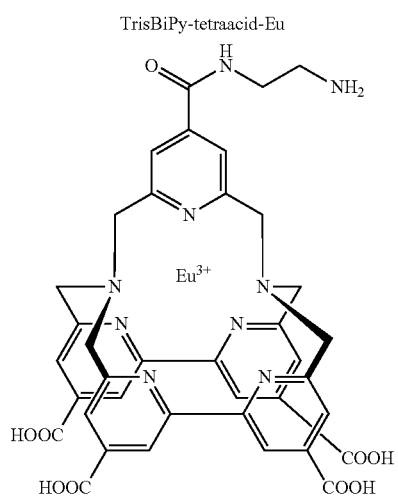

The chelates of lanthanides notably described in patents U.S. Pat. No. 4,761,481, U.S. Pat. No. 5,032,677, U.S. Pat. No. 5,055,578, U.S. Pat. No. 5,106,957, U.S. Pat. No. 5,116,989, U.S. Pat. No. 4,761,481, U.S. Pat. No. 4,801,722, U.S. Pat. No. 4,794,191, U.S. Pat. No. 4,637,988, U.S. Pat. No. 4,670,572, U.S. Pat. No. 4,837,169, U.S. Pat. No. 4,859,777. Patents EP 0 403 593, U.S. Pat. No. 5,324,825, U.S. Pat. No. 5,202,423, U.S. Pat. No. 5,316,909 describe chelates composed of a nonadentate ligand such as terpyridine. Chelates of lanthanides are marketed by the company PerkinElmer.

Complexes of lanthanides consisting of a chelating agent, such as tetraazacyclododecane, substituted with a chromophore comprising aromatic rings, such as those described by Poole R. et al. in Biomol. Chem., 2005, 3, 1013-1024 "Synthesis and characterization of highly emissive and kinetically stable lanthanide complexes suitable for usage in cellulo", can also be used. It is also possible to use the complexes described in application WO 2009/10580.

The cryptates of lanthanides described in patents EP 1 154 991 and EP 1 154 990 can also be used.

The terbium cryptate with the following formula (which can be coupled to a compound to be labeled via a reactive group, here for example an $NH_2$ group):

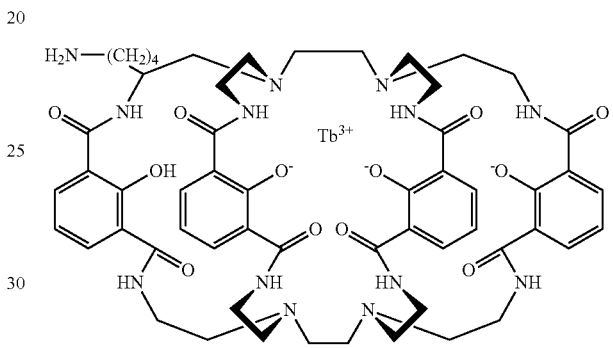

and whose synthesis is described in international application WO 2008/063721 (compound 6a page 89).

The terbium cryptate Lumi4-Tb from the company Lumiphore, marketed by Cisbio Bioassays.

The quantum dye from the company Research Organics, with the following formula (which can be coupled to the compound to be labeled via a reactive group, here NCS):

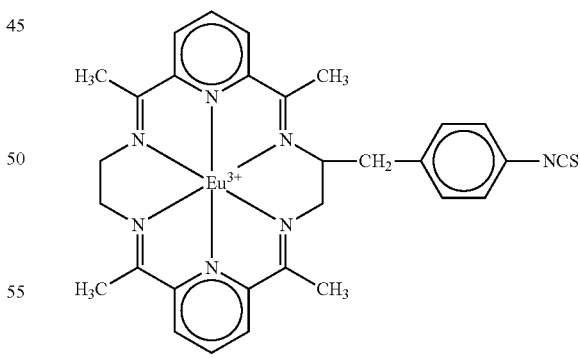

The chelates of ruthenium, in particular the complexes consisting of a ruthenium ion and several bipyridines such as ruthenium(II) tris(2,2'-bipyridine).

The terbium chelate DTPA-cs124 Tb, marketed by the company Life technologies with the following formula (which can be coupled to the compound to be labeled via a reactive group R) and whose synthesis is described in U.S. Pat. No. 5,622,821.

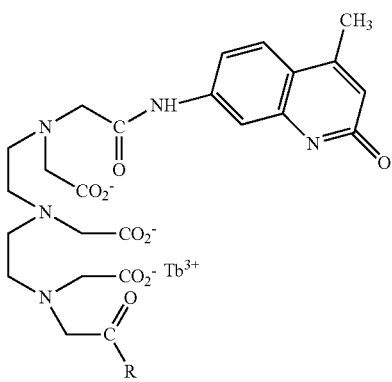

The terbium chelate of the following formula, described by Latva et al. (Journal of Luminescence 75: 149-169):

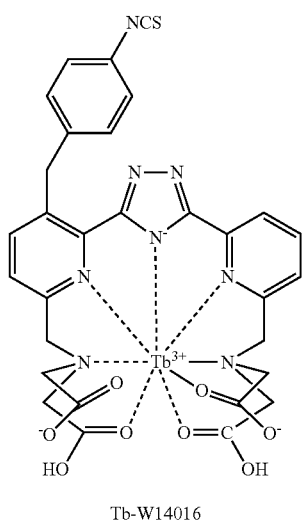

Tb-W14016

Particularly advantageously, the fluorescent donor compound is selected from: a europium cryptate; a europium chelate; a terbium chelate; a terbium cryptate; a ruthenium chelate; and a quantum dye; the europium and terbium chelates and cryptates being particularly preferred.

The complexes of dysprosium (Dy3+), of samarium (Sm3+), of neodymium (Nd3+), of ytterbium (Yb3+) or of erbium (Er3+) are also complexes of rare earths suitable for the purposes of the invention.

The fluorescent acceptor compounds can be selected from the following group: the allophycocyanins, in particular those known by the trade name XL665; luminescent organic molecules, such as rhodamines, cyanines (such as for example Cy5), squaraines, coumarins, proflavins, acridines, fluoresceins, derivatives of boron-dipyrromethene (marketed under the name "Bodipy"), the fluorophores known by the name "Atto", the fluorophores known by the name "DY", the compounds known by the name "Alexa", nitrobenzoxadiazole. Advantageously, the fluorescent acceptor compounds are selected from allophycocyanins, rhodamines, cyanines, squaraines, coumarins, proflavins, acridines, fluoresceins, derivatives of boron-dipyrromethene, nitrobenzoxadiazole.

The expressions "cyanines" and "rhodamines" must be understood respectively as "cyanine derivatives" and "rhodamine derivatives". A person skilled in the art knows these various fluorophores, which are commercially available.

The "Alexa" compounds are marketed by the company Invitrogen; the "Atto" compounds are marketed by the company Attotec; the "DY" compounds are marketed by the company Dyomics; the "Cy" compounds are marketed by the company Amersham Biosciences; the other compounds are marketed by various suppliers of chemical reagents, such as the companies Sigma, Aldrich or Acros.

The following fluorescent proteins can also be used as fluorescent acceptor compound: the cyan fluorescent proteins (AmCyan1, Midori-Ishi Cyan, mTFP1), the green fluorescent proteins (EGFP, AcGFP, TurboGFP, Emerald, Azami Green, ZsGreen), the yellow fluorescent proteins (EYFP, Topaz, Venus, mCitrine, YPet, PhiYFP, ZsYellow1, mBanana), the orange and red fluorescent proteins (Orange kusibari, mOrange, tdtomato, DsRed, DsRed2, DsRed-Express, DsRed-Monomer, mTangerine, AsRed2, mRFP1, JRed, mCherry, mStrawberry, HcRed1, mRaspberry, HcRed-Tandem, mPlim, AQ143), the fluorescent proteins in the far red (mKate, mKate2, tdKatushka2).

For the purposes of the invention, derivatives of cyanines or of fluorescein are preferred as fluorescent acceptor compounds.

Reagent Kits, Cells

The invention also relates to expression vectors and reagent kits for carrying out the methods according to the invention.

The expression vectors according to the invention are plasmids permitting expression of a fusion protein comprising the DNA sequence coding for the Fc receptor of interest and the sequence coding for a suicide enzyme, in particular selected from the mutants of dehalogenase, a fragment of the acyl transport protein or the mutants of 06-alkylguanine DNA alkyltransferase, the latter being preferred. They can be obtained by integrating the DNA sequence coding for the Fc receptor of interest in one of the plasmids marketed by the company Cisbio Bioassays under the names TAG-LITE®, SNAP-Tag®, CLIP-Tag® and Halo-Tag®.

The invention also relates to cells, notably mammalian cells, that have been transfected stably or transiently with the expression vectors according to the invention. The techniques for introducing expression vectors into the cells, such as electroporation or the use of lipofectamine, are known by a person skilled in the art. In a particularly advantageous aspect, these cells were incubated in the presence of the substrate of the suicide enzyme, conjugated with a member of a pair of FRET partners, and the Fc receptor that they express is thus labeled. These cells can be packaged in frozen form for easier storage and distribution to the users.

The kits of reagents according to the invention comprise the expression vectors or the above cells, accompanied by one or both members of a pair of FRET partners. These FRET partners can be conjugated with the substrate of the suicide enzyme, and/or conjugated with a reference antibody whose Fc fragment is capable of binding to the Fc receptors expressed by the cells.

Preferably, in the aforementioned plasmids and reagent kits, the receptor of interest is a gamma Fc receptor and in particular the CD16a receptor or a variant thereof.

EXAMPLES

Example 1: Material and Method

Figure 2:
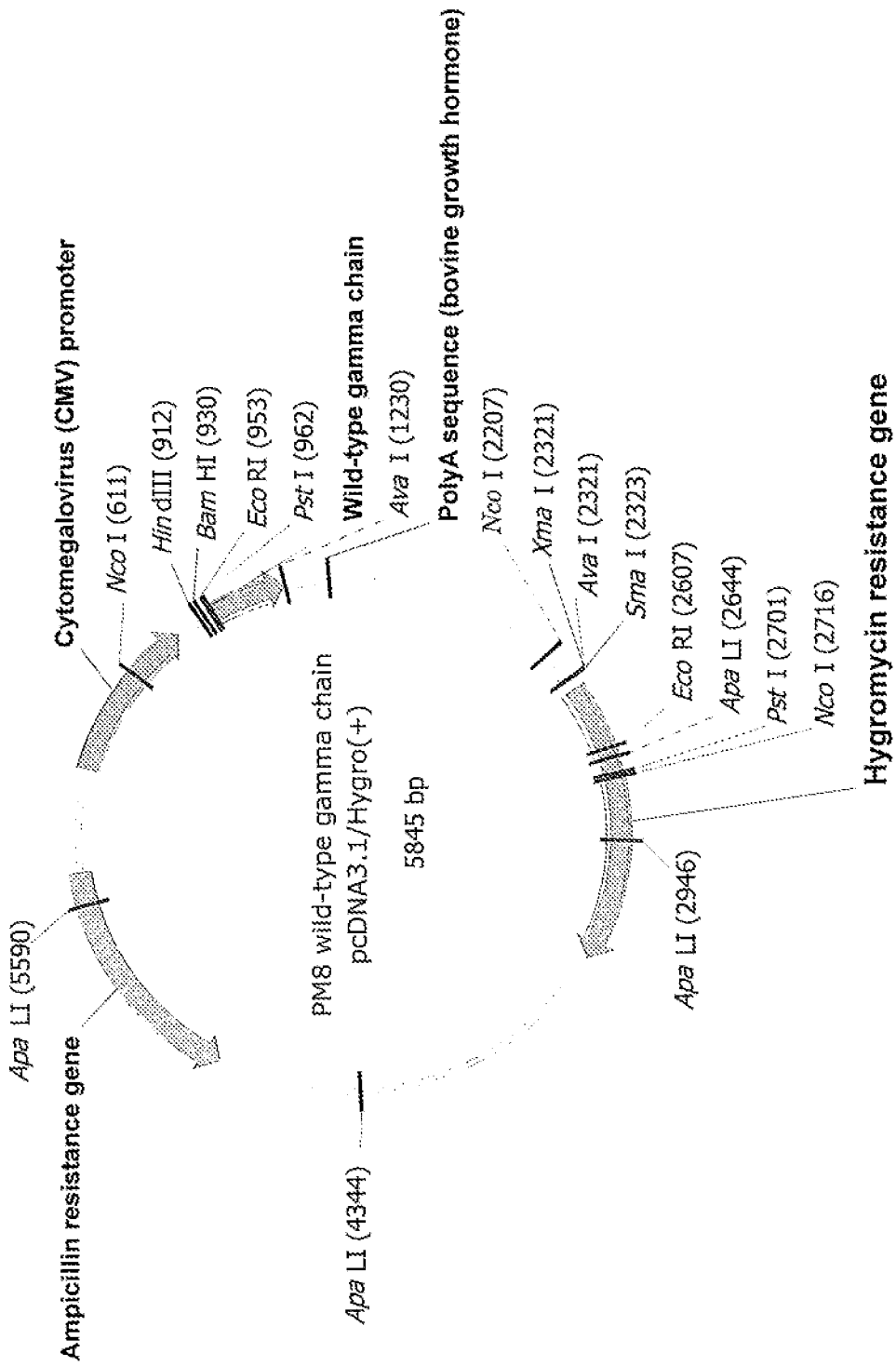
FIG. 2 is a plasmid coding wild-type gamma chain.

Reagents Used:
Culture medium: DMEM/Glutamax+10% FCS+streptomycin (50 µg/ml), penicillin 50 U/ml, HEPES 2 mM, nonessential amino acids 1% (InVitrogen)
OptiMEM: culture medium used for transfection, Invitrogen
Lipofectamine 2000: Invitrogen
SNAP-CD16A plasmid: prepared by inserting the nucleic acid sequence (SEQ ID No. 4) coding for the CD16a receptor (variant V158 (or V176) ref. Genbank NM_000569.6, protein sequence NP_000560.5) in the plasmid SNAP-Tag® pT8-SNAP-Neomycin (Cisbio Bioassays), see FIG. 1.
Plasmid gamma chain of the FcɛRI receptor: The DNA sequence (SEQ ID No. 5) coding for the gamma chain of the FcɛRI receptor was inserted in an expression plasmid by the classical techniques. The map of this plasmid is shown in FIG. 2. It is known that the CD16a receptor forms dimers with this gamma chain, and it is therefore recommended to coexpress the two proteins. The inventors nevertheless discovered that this coexpression was not necessary for carrying out the method according to the invention.
FCS: fetal calf serum, Invitrogen
DMSO: Dimethylsulfoxide, SIGMA
TAG-LITE® SNAP-Lumi4Tb: Donor compound, Cisbio Bioassays, ref. SSNPTBX
TAG-LITE®: labeling buffer, Cisbio Bioassays, ref. LABMED.
Transfection of the Cells:

A transfection mixture containing 5 µl of "SNAP-CD16A" plasmid (1 µg/µl), 15 µl of lipofectamine and 2.6 ml of OptiMEM medium and a mixture of 10 µl of "gamma chain" plasmid (1 µg/µl), 30 µl of lipofectamine and 5.4 ml of OptiMEM medium were incubated for 20 minutes at room temperature.

HEK293 cells were cultured in a T175 flask. Once these cells reached 60 to 70% confluence, the culture medium was removed and the cells were washed with 10 ml of PBS medium. 8 ml of the transfection mixture were then added to these cells, as well as 12 ml of culture medium. The cells were then incubated overnight at 37° C.
Labeling with the Fluorescent Donor Compound Lumi4®Tb After removal of the transfection mixture and washing with 10 ml of PBS, 10 ml of fluorescent donor compound TAG-LITE® SNAP-Lumi4-Tb (100 nM) in solution in the TAG-LITE® labeling buffer was added.

After incubation for 1 h at 37° C., the mixture was washed 4 times with the TAG-LITE® labeling buffer, then 5 ml of "cell dissociation buffer" (Sigma) were added for dissociating the cells as well as 5 ml of OptiMEM medium. The cells thus obtained were centrifuged for 5 min at 1200 rpm. The pellet was then resuspended with 1 ml+1 ml of TAG-LITE® labeling buffer to allow cell counting.

This suspension was centrifuged again for 5 min at 1200 rpm and the pellet was taken up in culture medium containing 10% FCS and 10% DMSO to obtain a suspension of labeled cells at a concentration of 1 million cells/ml.

This suspension was aliquoted into tubes at a rate of 1 ml per tube, and the tubes were put in a Nalgene box at −80° C.
Measurement of the FRET Signals In the following examples, the FRET signals were measured in resolved time on apparatus compatible with HTRF®, the PHERAstarFS (BMG Labtech) with a delay of 60 µs and an integration time of 400 µs.

Example 2

The cells prepared by the method described in example 1 were thawed at 37° C. and quickly mixed with 15 ml of PBS. The suspension obtained was centrifuged for 5 min at 1200 rpm and the supernatant was removed. The pellet was resuspended in TAG-LITE® buffer to obtain a suspension for distributing HEK-CD16a-Tb cells in the wells of a 384 LV multiwell plate at a concentration of 10 000 cells per well under 10 µl.

An unlabeled human antibody of IgG1 isotype (its epitope specificity is unimportant) was added at different final concentrations from 0.3 nM to 5 µM under 5 µl.

The same antibody, labeled with the d2 fluorophore acceptor (d2 labeling kit Cisbio Bioassays, ref. 62D2DPEA), was added at 200 nM under 5 µl for a final concentration of 50 nM.

The FRET signals emitted by the 384 plate were measured immediately, then after 30 min, 1 h, 2 h30, 3 h40, 5 h and 6 h.

Figure 3:
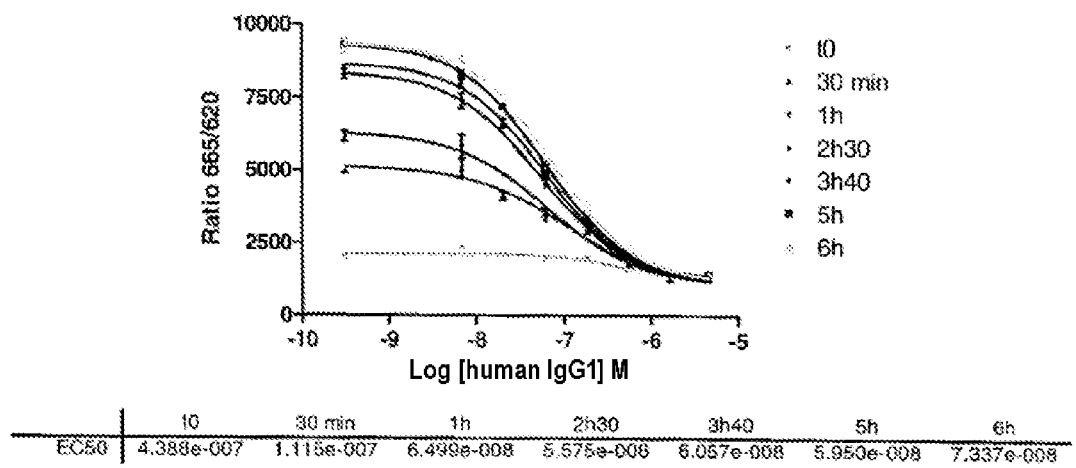
FIG. 3 is a graph depicting binding of the Fc fragment to CD16a: detection kinetics.

The results presented in FIG. 3 show that the method according to the invention allows effective monitoring of the kinetics of binding of the Fc fragment of an antibody to the CD16a receptors.

Example 3

Example 2 was reproduced but this time the unlabeled IgG1 antibody (competing antibody) was replaced with human antibodies of isotypes IgG2, IgG3 and IgG4 (their epitope specificities are unimportant), which are known not to have as good affinity for the receptor CD16a as the antibodies of the IgG1 type. After adding different concentrations of these antibodies, the reaction mixture was incubated for 4 h20.

Figure 4:
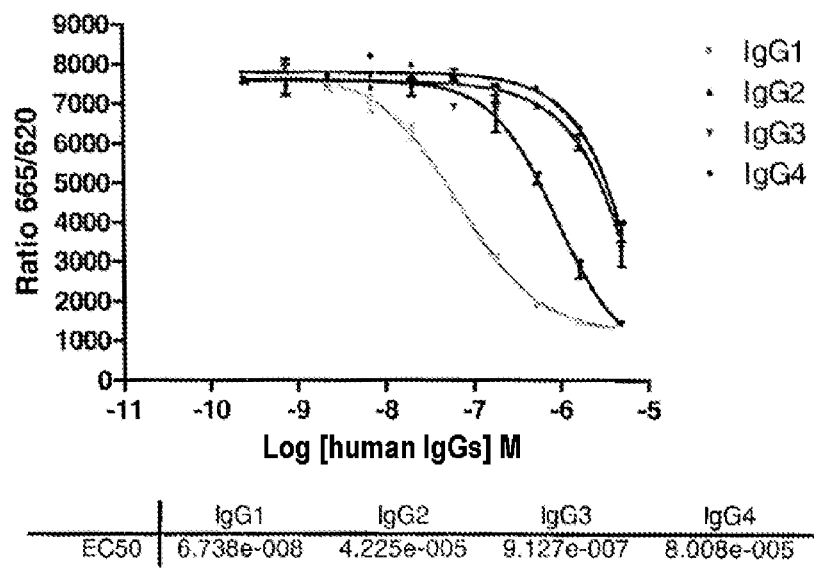
FIG. 4 is a graph depicting binding of the Fc fragment to CD16a for different isotypes.

The results presented in FIG. 4 confirm what was known in terms of affinity of IgG2, IgG3 and IgG4 for the CD16a receptor and therefore validate the method according to the invention, which allows effective comparison of a reference antibody with other antibodies and which is sufficiently sensitive to allow visualization of differences in affinity of these antibodies, here for the CD16a receptor.

Example 4

Example 2 was reproduced but this time the unlabeled IgG1 antibody (competing antibody) was replaced with different antibodies of the same subclass: Herceptin, pertuzumab and a mouse anti-EGFR antibody (ATCC528).

Figure 5:
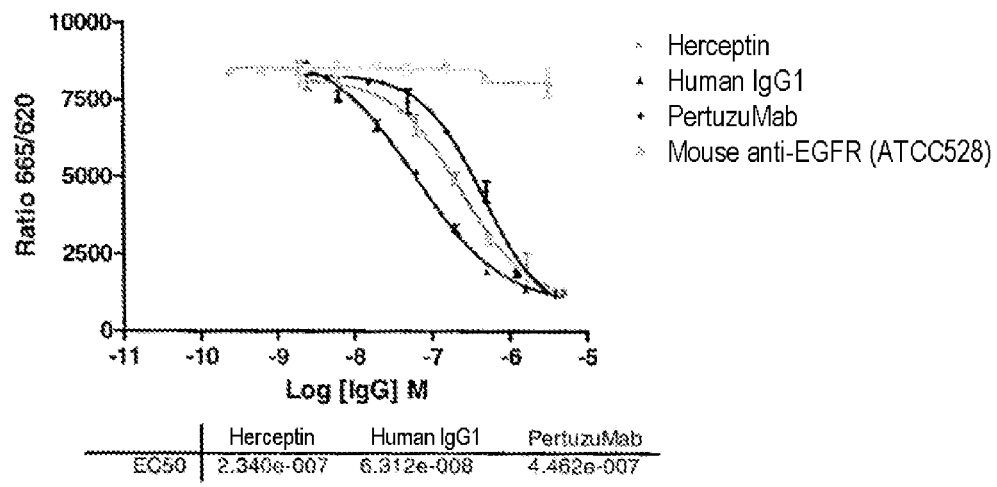
FIG. 5 is a graph depicting binding of the Fc fragment to CD16a with different IgGls.

The results presented in FIG. 5 confirm that the method according to the invention carried out with the CD16a receptor makes it possible to distinguish a mouse antibody, which does not bind to CD16a, from other human IgG1 antibodies, and is sufficiently sensitive for determining differences in affinity between several antibodies of the IgG1 class.

Example 5

The cells prepared by the method described in example 1 were thawed at 37° C. and quickly mixed with 15 ml of PBS. The suspension obtained was centrifuged for 5 min at 1200 rpm and the supernatant was removed. The pellet was resuspended in TAG-LITE® buffer to obtain a suspension for distributing HEK-CD16a-Tb cells in the wells of a 384 LV multiwell plate at a concentration of 10 000 cells per well under 10 µl.

A labeled human IgG1 antibody was added to each well at different concentrations for a final concentration from 1.5 to 300 nM, under 5 μl.

To measure the effect of nonspecific fixation of the labeled antibody on the cells, the unlabeled IgG1 antibody was also added at a final concentration of 3 μM under 5 μl, this volume being replaced with TAG-LITE® buffer to obtain the overall signal.

The specific signal is obtained by subtracting the nonspecific signal from the overall signal.

Figure 6:
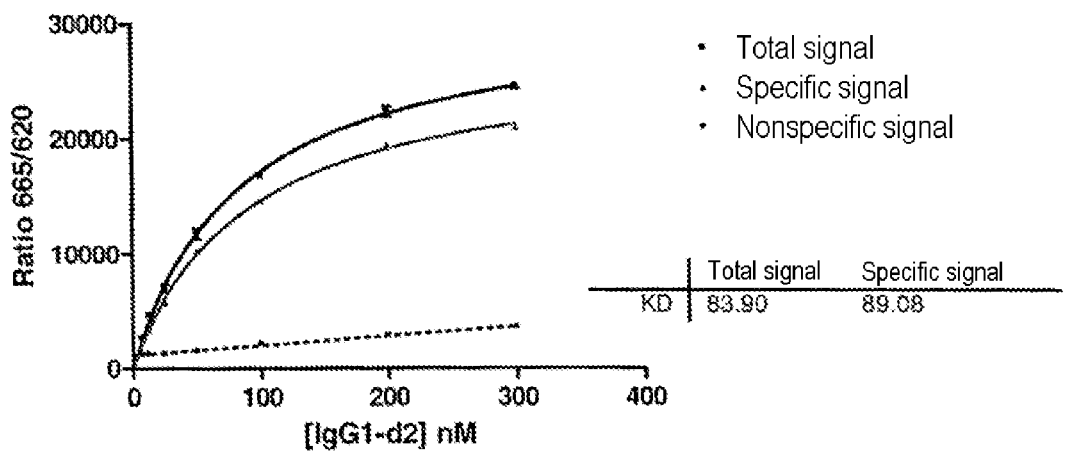
FIG. 6 is a graph depicting determination of Kd.

The FRET signals emitted by the 384 plate were measured at different times; the results after 20 h of incubation are presented in FIG. 6.

This example shows that the method according to the invention can be used for determining the dissociation constant of the IgG1-CD16a complex on living cells, and with a greatly reduced background noise.

Example 6

Fucosylation

Example 2 was reproduced but this time the unlabeled IgG1 antibody was replaced with different antibodies that had undergone treatment for removing the fucose residues (Ab1 which had undergone defucosylation of 4%, Ab2 which had undergone defucosylation of 8%, Ab3 which had undergone defucosylation of 57%, Ab4 which had undergone defucosylation of 11%, Ab5 which had undergone defucosylation of 80%).

After adding different concentrations of these antibodies, the reaction medium was incubated for 3 h30, and the plate was read on the Artemis 101 (Berthold technologies) in HTRF® mode.

Figure 7:
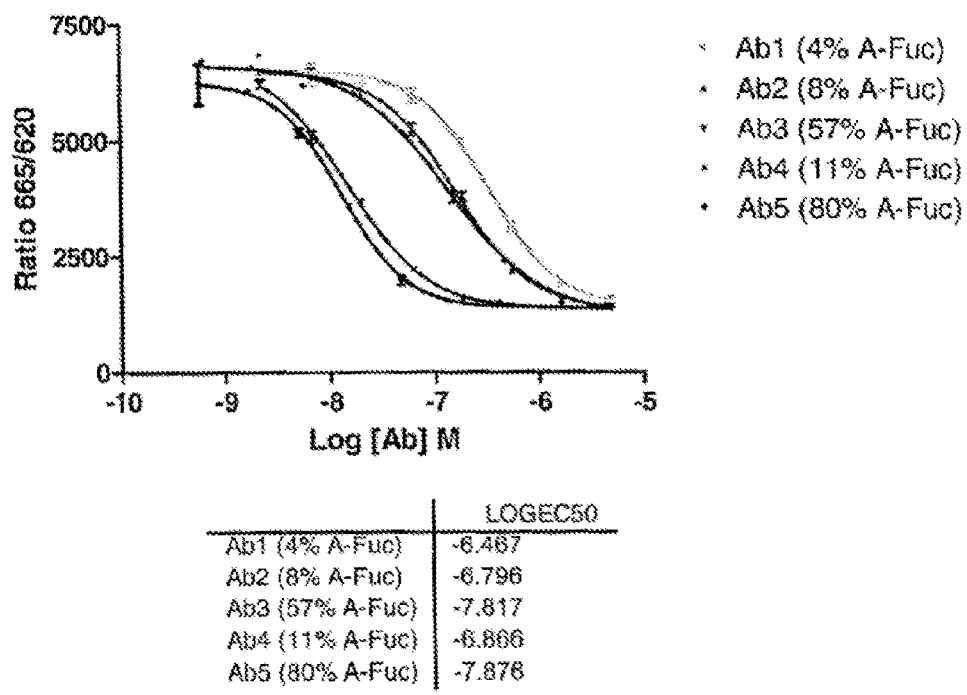
FIG. 7 is a graph depicting Affinity of Fc for CD16a as a function of the degree of fucosylation of the Ab.

It is known that defucosylation has the effect of increasing the affinity of the antibodies for the CD16a receptor, and this result is confirmed by FIG. 7, which also shows that the invention makes it possible, relatively simply, to evaluate the level of fucosylation of antibodies of interest from the results obtained with antibodies with known level of fucosylation. Moreover, this example also shows that the method according to the invention is sufficiently sensitive and makes it possible to determine differences in affinity between antibodies that have undergone various degrees of defucosylation.

The invention claimed is:

1. A method for determining a level of fucosylation of a test IgG antibody, comprising the following steps:
   (a) performing an in vitro cell based competitive binding of a plurality of competing IgG antibodies with an CD16a Fc receptor expressed in cell membranes or intact cells, to determine EC50 of each of the plurality of competing IgG antibodies, wherein the cell membranes or intact cells expressing the CD 16a Fc receptors are present in a measurement medium, wherein each of the plurality of competing IgG antibodies has known predetermined levels of fucosylation or of defucosylation, wherein the assay comprises:
      (i) labeling the CD16a Fc receptor with a first member of a pair of FRET partners, wherein the labeling is performed in the measurement medium or optionally introducing, into the medium, cell membranes or intact cells comprising labeled CD16a Fc receptors with the first member of a pair of FRET partners, wherein the labeling is direct or indirect,
      (ii) contacting the measurement medium comprising the labeled CD 16a Fc receptor of (i) with a fixed amount of a reference IgG antibody, labeled directly or indirectly with the second member of said pair of FRET partners, wherein the contacting occurs in the presence of different amounts of each of the plurality of competing IgG antibodies,
      (iii) measuring a FRET signal, wherein a decrease in the signal measured in the presence of each of the plurality of competing IgG antibodies relative to that measured in its absence indicates binding of competing IgG antibody to the CD16a Fc receptor,
      (iv) determining the level of EC50 for each of the plurality of competing IgG antibodies, and
      (v) correlating the EC50 of each of the plurality of competing IgG antibodies with its fucosylation levels;
   (b) repeating the assay of (a) comprising steps (i)-(iv), wherein the plurality of competing IgG antibodies are replaced by the test IgG antibody to determine EC50 of the test IgG antibody; and
   (c) assigning a level of fucosylation of the test IgG antibody by comparing its EC50 with that of the plurality of competing IgG antibodies having known predetermined levels of fucosylation or of defucosylation,
      wherein the IgG Fc amino acid sequence of each of the test IgG antibody, the plurality of competing IgG antibodies, and the reference IgG antibody has not been altered to affect the binding to the CD 16a Fc receptor.

* * * * *

SEQUENCE LISTING

```
<160> NUMBER OF SEQ ID NOS: 5

<210> SEQ ID NO 1
<211> LENGTH: 6
<212> TYPE: PRT
<213> ORGANISM: artificial sequence
<220> FEATURE:
<223> OTHER INFORMATION: binding partner
<220> FEATURE:
<221> NAME/KEY: misc_feature
<222> LOCATION: (3)..(4)
<223> OTHER INFORMATION: Xaa can be any naturally occurring amino acid

<400> SEQUENCE: 1

Cys Cys Xaa Xaa Cys Cys
1               5

<210> SEQ ID NO 2
<211> LENGTH: 8
<212> TYPE: PRT
<213> ORGANISM: artificial sequence
<220> FEATURE:
<223> OTHER INFORMATION: tag/antitag pair

<400> SEQUENCE: 2

Asp Tyr Lys Asp Asp Asp Asp Lys
1               5

<210> SEQ ID NO 3
<211> LENGTH: 9
<212> TYPE: PRT
<213> ORGANISM: artificial sequence
<220> FEATURE:
<223> OTHER INFORMATION: tag/antitag pair

<400> SEQUENCE: 3

Tyr Pro Tyr Asp Val Pro Phe Tyr Ala
1               5

<210> SEQ ID NO 4
<211> LENGTH: 6758
<212> TYPE: DNA
<213> ORGANISM: artificial sequence
```

```
<220> FEATURE:
<223> OTHER INFORMATION: plasmide
<220> FEATURE:
<221> NAME/KEY: promoter
<222> LOCATION: (232)..(819)
<223> OTHER INFORMATION: promoteur CMV
<220> FEATURE:
<221> NAME/KEY: sig_peptide
<222> LOCATION: (923)..(986)
<220> FEATURE:
<221> NAME/KEY: misc_feature
<222> LOCATION: (1004)..(1027)
<223> OTHER INFORMATION: QC tag
<220> FEATURE:
<221> NAME/KEY: misc_feature
<222> LOCATION: (1046)..(1591)
<223> OTHER INFORMATION: Snap tag
<220> FEATURE:
<221> NAME/KEY: gene
<222> LOCATION: (1610)..(2321)
<223> OTHER INFORMATION: gene d'interet
<220> FEATURE:
<221> NAME/KEY: polyA_site
<222> LOCATION: (2358)..(2582)
<223> OTHER INFORMATION: polyA BGH
<220> FEATURE:
<221> NAME/KEY: misc_feature
<222> LOCATION: (3466)..(4260)
<223> OTHER INFORMATION: Neo R
<220> FEATURE:
<221> NAME/KEY: misc_feature
<222> LOCATION: (5762)..(6622)
<223> OTHER INFORMATION: Ampi R

<400> SEQUENCE: 4
gacggatcgg gagatctccc gatccctat  ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta caaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagctttgag acatggcctt accagtgacc gccttgctcc tgccgctggc     960
cttgctgctc cacgccgcca ggccggccgc cgctagcggc atcgactaca aggacgacga    1020
tgacaaggcc ggcatcgatg ccatcatgga caaagactgc gaaatgaagc gcaccaccct    1080
ggatagccct ctgggcaagc tggaactgtc tgggtgcgaa cagggcctgc acgagatcaa    1140
gctgctgggc aaaggaacat ctgccgccga cgccgtggaa gtgcctgccc agccgccgt     1200 gctgggcgga ccagagccac tgatgcaggc caccgcctgg ctcaacgcct actttcacca    1260
gcctgaggcc atcgaggagt ccctgtgcc agccctgcac acccagtgt tccagcagga     1320
```

```
gagctttacc cgccaggtgc tgtggaaact gctgaaagtg gtgaagttcg gagaggtcat    1380
cagctaccag cagctggccg ccctggccgg caatcccgcc gccaccgccg ccgtgaaaac    1440
cgccctgagc ggaaatcccg tgcccattct gatccctgc caccgggtgg tgtctagctc    1500
tggcgccgtg gggggctacg agggcgggct cgccgtgaaa gagtggctgc tggcccacga    1560
gggccacaga ctgggcaagc ctgggctggg tgatatccag cacagtggcg gccgcgaaga    1620
tctcccaaag gctgtggtgt tcctggagcc tcaatggtac agggtgctcg agaaggacag    1680
tgtgactctg aagtgccagg gagcctactc ccctgaggac aattccacac agtggtttca    1740
caatgagagc ctcatctcaa gccaggcctc gagctacttc attgacgctg ccacagtcga    1800
cgacagtgga gagtacaggt gccagacaaa cctctccacc ctcagtgacc cggtgcagct    1860
agaagtccat atcggctggc tgttgctcca ggcccctcgg tgggtgttca aggaggaaga    1920
ccctattcac ctgaggtgtc acagctggaa gaacactgct ctgcataagg tcacatattt    1980
acagaatggc aaaggcagga agtattttca tcataattct gacttctaca ttccaaaagc    2040
cacactcaaa gacagcggct cctacttctg caggggcctt gtcgggagta aaaatgtgtc    2100
ttcagagact gtgaacatca ccatcactca aggtttggca gtgtcaacca tctcatcatt    2160 cttttccacct gggtaccaag tctctttctg cttggtgatg gtactccttt ttgcagtgga    2220
cacaggacta tatttctctg tgaagacaaa cattcgaagc tcaacaagag actggaagga    2280
ccataaattt aaatggagaa aggaccctca agacaaatga tctagagggc cgtttaaac    2340 ccgctgatca gcctcgactg tgccttctag ttgccagcca tctgttgttt gcccctcccc    2400
cgtgccttcc ttgaccctgg aaggtgccac tcccactgtc ctttcctaat aaaatgagga    2460
aattgcatcg cattgtctga gtaggtgtca ttctattctg ggggtgggg tgggcagga    2520 cagcaagggg gaggattggg aagacaatag caggcatgct ggggatgcgg tgggctctat    2580
ggcttctgag gcgaaagaa ccagctgggg ctctagggg tatccccacg cgccctgtag    2640
cggcgcatta agcgcggcgg gtgtggtggt tacgcgcagc gtgaccgcta cacttgccag    2700
cgccctagcg cccgctcctt tcgctttctt cccttccttt ctcgccacgt tcgccggctt    2760
tccccgtcaa gctctaaatc gggggctccc tttagggttc cgatttagtg ctttacggca    2820
cctcgacccc aaaaaacttg attagggtga tggttcacgt agtgggccat cgccctgata    2880
gacggttttt cgccctttga cgttggagtc acgttctttt aatagtggac tcttgttcca    2940
aactggaaca acactcaacc ctatctcggt ctattctttt gatttataag gattttgcc    3000 gatttcggcc tattggttaa aaaatgagct gatttaacaa aaatttaacg cgaattaatt    3060
ctgtggaatg tgtgtcagtt agggtgtgga aagtccccag gctccccagc aggcagaagt    3120
atgcaaagca tgcatctcaa ttagtcagca accaggtgtg gaaagtcccc aggctcccca    3180
gcaggcagaa gtatgcaaag catgcatctc aattagtcag caaccatagt cccgccccta    3240
actccgccca tcccgcccct aactccgccc agttccgccc attctccgcc ccatggctga    3300 ctaattttttt ttatttatgc agaggccgag gccgcctctg cctctgagct attccagaag    3360
tagtgaggag gctttttggg aggcctaggc ttttgcaaaa agctcccggg agcttgtata    3420
tccattttcg gatctgatca agagacagga tgaggatcgt ttcgcatgat tgaacaagat    3480
ggattgcacg caggttctcc ggccgcttgg gtggagaggc tattcggcta tgactgggca    3540
caacagacaa tcggctgctc tgatgccgcc gtgttccggc tgtcagcgca ggggcgcccg    3600 gttcttttg tcaagaccga cctgtccggt gccctgaatg aactgcagga cgaggcagcg    3660
```

```
cggctatcgt ggctggccac gacgggcgtt ccttgcgcag ctgtgctcga cgttgtcact    3720
gaagcgggaa gggactggct gctattgggc gaagtgccgg ggcaggatct cctgtcatct    3780
caccttgctc ctgccgagaa agtatccatc atggctgatg caatgcggcg gctgcatacg    3840
cttgatccgg ctacctgccc attcgaccac caagcgaaac atcgcatcga gcgagcacgt    3900
actcggatgg aagccggtct tgtcgatcag gatgatctgg acgaagagca tcaggggctc    3960
gcgccagccg aactgttcgc caggctcaag gcgcgcatgc ccgacggcga ggatctcgtc    4020
gtgacccatg gcgatgcctg cttgccgaat atcatggtgg aaaatggccg cttttctgga    4080
ttcatcgact gtggccggct gggtgtggcg gaccgctatc aggacatagc gttggctacc    4140
cgtgatattg ctgaagagct tggcggcgaa tgggctgacc gcttcctcgt gctttacggt    4200
atcgccgctc ccgattcgca gcgcatcgcc ttctatcgcc ttcttgacga gttcttctga    4260
gcgggactct ggggttcgaa atgaccgacc aagcgacgcc caacctgcca tcacgagatt    4320
tcgattccac cgccgccttc tatgaaaggt tgggcttcgg aatcgttttc cgggacgccg    4380
gctggatgat cctccagcgc ggggatctca tgctggagtt cttcgccac cccaacttgt     4440 ttattgcagc ttataatggt tacaaataaa gcaatagcat cacaaatttc acaaataaag    4500
catttttttc actgcattct agttgtggtt tgtccaaact catcaatgta tcttatcatg    4560
tctgtatacc gtcgacctct agctagagct tggcgtaatc atggtcatag ctgtttcctg    4620
tgtgaaattg ttatccgctc acaattccac acaacatacg agccgaagc ataaagtgta     4680 aagcctgggg tgcctaatga gtgagctaac tcacattaat tgcgttgcgc tcactgcccg    4740
ctttccagtc gggaaacctg tcgtgccagc tgcattaatg aatcggccaa cgcgcgggga    4800
gaggcggttt gcgtattggg cgctcttccg cttcctcgct cactgactcg ctgcgctcgg    4860
tcgttcggct gcggcgagcg gtatcagctc actcaaaggc ggtaatacgg ttatccacag    4920
aatcagggga taacgcagga aagaacatgt gagcaaaagg ccagcaaaag gccaggaacc    4980
gtaaaaaggc cgcgttgctg gcgttttttcc ataggctccg cccccctgac gagcatcaca    5040
aaaatcgacg ctcaagtcag aggtggcgaa acccgacagg actataaaga taccaggcgt    5100
ttccccctgg aagctccctc gtgcgctctc ctgttccgac cctgccgctt accggatacc    5160
tgtccgcctt tctcccttcg ggaagcgtgg cgctttctca tagctcacgc tgtaggtatc    5220
tcagttcggt gtaggtcgtt cgctccaagc tgggctgtgt gcacgaaccc cccgttcagc    5280
ccgaccgctg cgccttatcc ggtaactatc gtcttgagtc aacccggta agacacgact    5340 tatcgccact ggcagcagcc actggtaaca ggattagcag agcgaggtat gtaggcggtg    5400
ctacagagtt cttgaagtgg tggcctaact acggctacac tagaagaaca gtatttggta    5460
tctgcgctct gctgaagcca gttaccttcg gaaaaagagt tggtagctct tgatccggca    5520
aacaaaccac cgctggtagc ggttttttttg tttgcaagca gcagattacg cgcagaaaaa    5580
aaggatctca agaagatcct ttgatctttt ctacggggtc tgacgctcag tggaacgaaa    5640
actcacgtta agggattttg gtcatgagat tatcaaaaag gatcttcacc tagatccttt    5700
taaattaaaa atgaagtttt aaatcaatct aaagtatata tgagtaaact tggtctgaca    5760
gttaccaatg cttaatcagt gaggcaccta tctcagcgat ctgtctattt cgttcatcca    5820
tagttgcctg actccccgtc gtgtagataa ctacgatacg ggagggctta ccatctggcc    5880
ccagtgctgc aatgataccg cgagacccac gctcaccggc tccagattta tcagcaataa    5940
accagccagc cggaagggcc gagcgcagaa gtggtcctgc aactttatcc gcctccatcc    6000
agtctattaa ttgttgccgg gaagctagag taagtagttc gccagttaat agtttgcgca    6060
```

| | | |
|---|---|---|
| acgttgttgc cattgctaca ggcatcgtgg tgtcacgctc gtcgtttggt atggcttcat | 6120 |
| tcagctccgg ttcccaacga tcaaggcgag ttacatgatc ccccatgttg tgcaaaaaag | 6180 |
| cggttagctc cttcggtcct ccgatcgttg tcagaagtaa gttggccgca gtgttatcac | 6240 |
| tcatggttat ggcagcactg cataattctc ttactgtcat gccatccgta agatgctttt | 6300 |
| ctgtgactgg tgagtactca accaagtcat tctgagaata gtgtatgcgg cgaccgagtt | 6360 |
| gctcttgccc ggcgtcaata cgggataata ccgcgccaca tagcagaact ttaaaagtgc | 6420 |
| tcatcattgg aaaacgttct cggggcgaaa actctcaag gatcttaccg ctgttgagat | 6480 |
| ccagttcgat gtaacccact cgtgcaccca actgatcttc agcatctttt actttcacca | 6540 |
| gcgtttctgg gtgagcaaaa acaggaaggc aaaatgccgc aaaaaaggga ataagggcga | 6600 |
| cacggaaatg ttgaatactc atactcttcc ttttcaata ttattgaagc atttatcagg | 6660 |
| gttattgtct catgagcgga tacatatttg aatgtattta gaaaaataaa caaatagggg | 6720 |
| ttccgcgcac atttccccga aaagtgccac ctgacgtc | 6758 |

```
<210> SEQ ID NO 5
<211> LENGTH: 5845
<212> TYPE: DNA
<213> ORGANISM: artificial sequence
<220> FEATURE:
<223> OTHER INFORMATION: plasmid
<220> FEATURE:
<221> NAME/KEY: promoter
<222> LOCATION: (232)..(819)
<223> OTHER INFORMATION: promoteur CMV
<220> FEATURE:
<221> NAME/KEY: gene
<222> LOCATION: (965)..(1229)
<220> FEATURE:
<221> NAME/KEY: polyA_site
<222> LOCATION: (1272)..(1496)
<223> OTHER INFORMATION: polyA BGH
<220> FEATURE:
<221> NAME/KEY: misc_feature
<222> LOCATION: (2363)..(3388)
<223> OTHER INFORMATION: Hygro R
<220> FEATURE:
<221> NAME/KEY: misc_feature
<222> LOCATION: (4849)..(5709)
<223> OTHER INFORMATION: Ampi R

<400> SEQUENCE: 5
```

| | | |
|---|---|---|
| gacggatcgg gagatctccc gatcccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |

```
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattctgc    960
agatatcatg attccagcag tggtcttgct cttactcctt ttggttgaac aagcagcggc   1020
cctgggagag cctcagctct gctatatcct ggatgccatc ctgtttctgt atggaattgt   1080
cctcaccctc ctctactgtc gactgaagat ccaagtgcga aaggcagcta taaccagcta   1140
tgagaaatca gatggtgttt acacgggcct gagcaccagg aaccaggaga cttacgagac   1200
tctgaagcat gagaaaccac cacagtagct cgagtctaga gggcccgttt aaacccgctg   1260
atcagcctcg actgtgcctt ctagttgcca gccatctgtt gtttgcccct cccccgtgcc   1320
ttccttgacc ctggaaggtg ccactcccac tgtcctttcc taataaaatg aggaaattgc   1380
atcgcattgt ctgagtaggt gtcattctat tctggggggt ggggtggggc aggacagcaa   1440
gggggaggat tgggaagaca atagcaggca tgctggggat gcggtgggct ctatggcttc   1500
tgaggcggaa agaaccagct ggggctctag gggtatcccc acgcgccct gtagcggcgc    1560 attaagcgcg gcgggtgtgg tggttacgcg cagcgtgacc gctacacttg ccagcgccct   1620
agcgcccgct cctttcgctt tcttcccttc ctttctcgcc acgttcgccg gctttccccg   1680
tcaagctcta aatcggggca tccctttagg gttccgattt agtgctttac ggcacctcga   1740
ccccaaaaaa cttgattagg gtgatggttc acgtagtggg ccatcgccct gatagacggt   1800
ttttcgccct ttgacgttgg agtccacgtt ctttaatagt ggactcttgt tccaaactgg   1860
aacaacactc aaccctatct cggtctattc ttttgattta agggatttt gggatttc     1920 ggcctattgg ttaaaaaatg agctgattta acaaaaattt aacgcgaatt aattctgtgg   1980
aatgtgtgtc agttagggtg tggaaagtcc ccaggctccc caggcaggca gaagtatgca   2040
aagcatgcat ctcaattagt cagcaaccag gtgtggaaag tccccaggct ccccagcagg   2100
cagaagtatg caaagcatgc atctcaatta gtcagcaacc atagtcccgc ccctaactcc   2160
gcccatcccg cccctaactc cgcccagttc cgcccattct ccgccccatg gctgactaat   2220 ttttttttatt tatgcagagg ccgaggccgc ctctgcctct gagctattcc agaagtagtg   2280
aggaggcttt tttggaggcc taggcttttg caaaaagctc ccgggagctt gtatatccat   2340
tttcggatct gatcagcacg tgatgaaaaa gcctgaactc accgcgacgt ctgtcgagaa   2400
gtttctgatc gaaaagttcg acagcgtctc cgacctgatg cagctctcgg agggcgaaga   2460
atctcgtgct ttcagcttcg atgtaggagg gcgtggatat gtcctgcggg taaatagctg   2520
cgccgatggt ttctacaaag atcgttatgt ttatcggcac tttgcatcgg ccgcgctccc   2580
gattccggaa gtgcttgaca ttggggaatt cagcgagagc ctgacctatt gcatctcccg   2640
ccgtgcacag ggtgtcacgt tgcaagacct gcctgaaacc gaactgcccg ctgttctgca   2700
gccggtcgcg gaggccatgg atgcgatcgc tgcggccgat cttagccaga cgagcgggtt   2760
cggcccattc ggaccgcaag gaatcggtca atacactaca tggcgtgatt tcatatgcgc   2820
gattgctgat ccccatgtgt atcactggca aactgtgatg gacgacaccg tcagtgcgtc   2880
cgtcgcgcag gctctcgatg agctgatgct ttgggccgag gactgccccg aagtccggca   2940
cctcgtgcac gcggatttcg gctccaacaa tgtcctgacg gacaatggcc gcataacagc   3000
ggtcattgac tggagcgagg cgatgttcgg ggattcccaa tacgaggtcg ccaacatctt   3060
cttctggagg ccgtggttgg cttgtatgga gcagcagacg cgctacttcg agcggaggca   3120
```

```
tccggagctt gcaggatcgc cgcggctccg ggcgtatatg ctccgcattg gtcttgacca   3180
actctatcag agcttggttg acggcaattt cgatgatgca gcttgggcgc agggtcgatg   3240
cgacgcaatc gtccgatccg gagccgggac tgtcgggcgt acacaaatcg cccgcagaag   3300
cgcggccgtc tggaccgatg gctgtgtaga agtactcgcc gatagtggaa accgacgccc   3360
cagcactcgt ccgagggcaa aggaatagca cgtgctacga gatttcgatt ccaccgccgc   3420
cttctatgaa aggttgggct tcggaatcgt tttccgggac gccggctgga tgatcctcca   3480
gcgcggggat ctcatgctgg agttcttcgc ccaccccaac ttgtttattg cagcttataa   3540
tggttacaaa taaagcaata gcatcacaaa tttcacaaat aaagcatttt tttcactgca   3600
ttctagttgt ggtttgtcca aactcatcaa tgtatcttat catgtctgta taccgtcgac   3660
ctctagctag agcttggcgt aatcatggtc atagctgttt cctgtgtgaa attgttatcc   3720
gctcacaatt ccacacaaca tacgagccgg aagcataaag tgtaaagcct ggggtgccta   3780
atgagtgagc taactcacat taattgcgtt gcgctcactg cccgctttcc agtcgggaaa   3840
cctgtcgtgc cagctgcatt aatgaatcgg ccaacgcgcg gggagaggcg gtttgcgtat   3900
tgggcgctct tccgcttcct cgctcactga ctcgctgcgc tcggtcgttc ggctgcggcg   3960
agcggtatca gctcactcaa aggcggtaat acggttatcc acagaatcag gggataacgc   4020
aggaaagaac atgtgagcaa aaggccagca aaaggccagg aaccgtaaaa aggccgcgtt   4080
gctggcgttt ttccataggc tccgcccccc tgacgagcat cacaaaaatc gacgctcaag   4140
tcagaggtgg cgaaacccga caggactata agataccag gcgtttcccc ctggaagctc   4200
cctcgtgcgc tctcctgttc cgaccctgcc gcttaccgga tacctgtccg cctttctccc   4260
ttcgggaagc gtggcgcttt ctcaatgctc acgctgtagg tatctcagtt cggtgtaggt   4320
cgttcgctcc aagctgggct gtgtgcacga accccccgtt cagcccgacc gctgcgcctt   4380
atccggtaac tatcgtcttg agtccaaccc ggtaagacac gacttatcgc cactggcagc   4440
agccactggt aacaggatta gcagagcgag gtatgtaggc ggtgctacag agttcttgaa   4500
gtggtggcct aactacggct acactagaag gacagtattt ggtatctgcg ctctgctgaa   4560
gccagttacc ttcggaaaaa gagttggtag ctcttgatcc ggcaaacaaa ccaccgctgg   4620
tagcggtggt ttttttgttt gcaagcagca gattacgcgc agaaaaaaag gatctcaaga   4680
agatcctttg atcttttcta cggggtctga cgctcagtgg aacgaaaact cacgttaagg   4740
gattttggtc atgagattat caaaaaggat cttcacctag atccttttaa attaaaaatg   4800
aagttttaaa tcaatctaaa gtatatatga gtaaacttgg tctgacagtt accaatgctt   4860
aatcagtgag gcacctatct cagcgatctg tctatttcgt tcatccatag ttgcctgact   4920
ccccgtcgtg tagataacta cgatacggga gggcttacca tctggcccca gtgctgcaat   4980
gataccgcga gacccacgct caccggctcc agatttatca gcaataaacc agccagccgg   5040
aagggccgag cgcagaagtg gtcctgcaac tttatccgcc tccatccagt ctattaattg   5100
ttgccgggaa gctagagtaa gtagttcgcc agttaatagt ttgcgcaacg ttgttgccat   5160
tgctacaggc atcgtggtgt cacgctcgtc gtttggtatg gcttcattca gctccggttc   5220
ccaacgatca aggcgagtta catgatcccc catgttgtgc aaaaaagcgg ttagctcctt   5280
cggtcctccg atcgttgtca gaagtaagtt ggccgcagtg ttatcactca tggttatggc   5340
agcactgcat aattctctta ctgtcatgcc atccgtaaga tgcttttctg tgactggtga   5400
gtactcaacc aagtcattct gagaatagtg tatgcggcga ccgagttgct cttgcccggc   5460
gtcaatacgg gataataccg cgccacatag cagaacttta aaagtgctca tcattggaaa   5520
```

```
acgttcttcg gggcgaaaac tctcaaggat cttaccgctg ttgagatcca gttcgatgta    5580
acccactcgt gcacccaact gatcttcagc atcttttact ttcaccagcg tttctgggtg    5640
agcaaaaaca ggaaggcaaa atgccgcaaa aaagggaata agggcgacac ggaaatgttg    5700
aatactcata ctcttccttt ttcaatatta ttgaagcatt tatcagggtt attgtctcat    5760
gagcggatac atatttgaat gtatttagaa aaataaacaa atagggggttc cgcgcacatt    5820 tccccgaaaa gtgccacctg acgtc                                           5845
```